United States Patent [19]

Hulsey

[11] Patent Number: 4,496,317
[45] Date of Patent: Jan. 29, 1985

[54] ADJUSTABLE ORTHODONTIC APPLIANCE

[76] Inventor: Charles M. Hulsey, 911 E. Valley Parkway, Escondido, Calif. 92025

[21] Appl. No.: 507,731

[22] Filed: Jun. 27, 1983

[51] Int. Cl.³ .................................................. A61C 7/00
[52] U.S. Cl. ........................................ 433/10; 433/16
[58] Field of Search ................................ 433/16, 8, 12

[56] References Cited

U.S. PATENT DOCUMENTS

| 2,104,192 | 1/1938 | Ford | 433/10 |
|---|---|---|---|
| 2,921,371 | 1/1960 | Wallshein | 433/13 |
| 3,028,671 | 4/1962 | Berger | 433/8 |
| 3,238,619 | 3/1966 | Brunson et al. | 433/13 |
| 3,262,207 | 7/1966 | Kesling | 433/18 |
| 3,683,502 | 8/1972 | Wallshein | 433/22 |
| 4,077,126 | 3/1978 | Pletcher | 433/10 |
| 4,196,517 | 4/1980 | Forster | 433/17 |
| 4,243,387 | 1/1981 | Prins | 433/16 |

Primary Examiner—Robert Peshock
Attorney, Agent, or Firm—Baker, Maxham, Callan & Jester

[57] ABSTRACT

An orthodontic appliance for attachment to a tooth for attachment of arch wires and the like includes a base member for attachment to a tooth with an elongated arm extending from the base member for extending parallel to the tooth axis and including an attachment bracket that is adjustably mounted on the arm for positioning at or beyond the gum line of the tooth.

13 Claims, 7 Drawing Figures

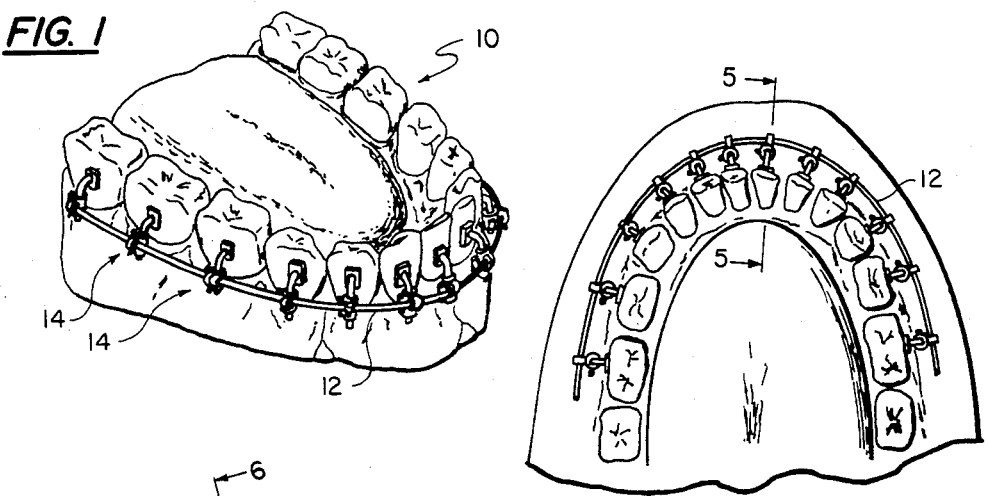
FIG. 1
FIG. 2
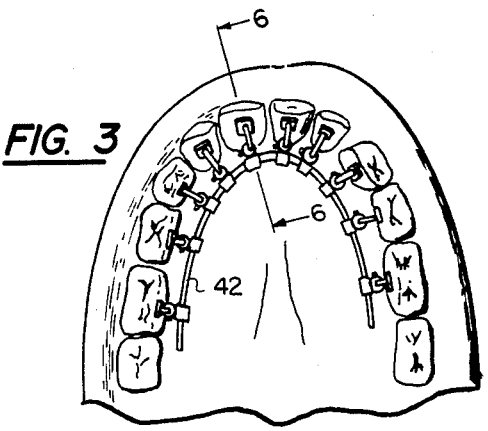
FIG. 3
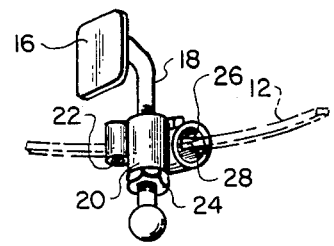
FIG. 4
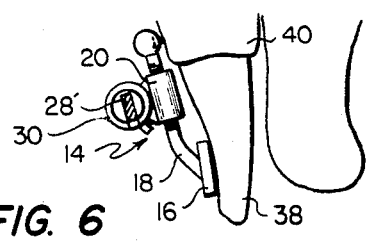
FIG. 6
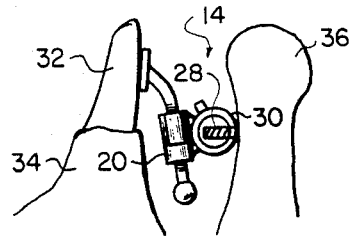
FIG. 5
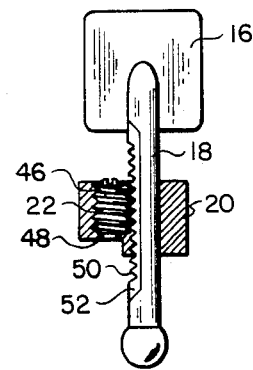
FIG. 7

ADJUSTABLE ORTHODONTIC APPLIANCE

BACKGROUND OF THE INVENTION

The present invention relates to orthodontic devices and pertains particularly to an improved orthodontic bracket.

Orthodontic brackets attachable to teeth for the application of positioning and aligning forces to the teeth are widely known. These brackets take many forms and include attaching clamps for the attachment of arch wires and the like. The brackets are typically attached and positioned on the crown of the tooth with the arch wires extending across the crown of the teeth. Such brackets and appliances are commonly used to apply a force to teeth for forcing them into correct alignment and orientation. By the application of proper force it is possible to shift, tip or rotate a tooth in any desired direction of position.

Such prior known brackets, however, are objectionable for a number of reasons. One of the objectionable traits of prior known brackets is the positioning of the tension wires across the crown of the teeth. This positions the tensioning wires in a position to be not only unsightly but to interfere with chewing and the like.

Additionally, it is frequently desirable that the force be applied along or about an axis that is displaced from the crown of the tooth.

It is therefore desirable that an improved orthodontic appliance be available which positions the attachment bracket for tension wires and the like at a position away from the crown of the tooth.

SUMMARY AND OBJECTS OF THE INVENTION

It is therefore the primary object of the present invention to provide an improved orthodontic appliance.

In accordance with the primary aspect of the present invention an orthodontic appliance includes a base member for attachment to a tooth with an elongated arm attached to the base and positioned for extending parallel to the axis of the tooth for positioning an adjustable attachment clamp on the outer end thereof away from the crown of the tooth.

BRIEF DESCRIPTION OF THE DRAWINGS

The above and other objects and advantages of the present invention will become apparent from the following description when read in conjunction with the drawings wherein:

FIG. 1 is a perspective view showing an installation in accordance with the invention.

FIG. 2 is a top plan view of the labial installation of FIG. 1.

FIG. 3 is a plan view of a lingual installation.

FIG. 4 is a detailed view of an orthopedic bracket in accordance with the invention.

FIG. 5 is a view generally on line 5—5 of FIG. 2.

FIG. 6 is a view taken generally on line 6—6 of FIG. 3.

FIG. 7 is a view with portions broken away to show details of the adjustment drive.

DETAILED DESCRIPTION OF A PREFERRED EMBODIMENT

Referring to the drawings particularly FIG. 1, the teeth of a lower jaw of a mouth are designated generally by the numeral 10 and are shown equipped with an orthodontic appliance structure including a tension or arch wire 12 which is attached to a plurality of individual brackets designated generally by the numeral 14. The individual brackets are each attached to individual teeth in the lower jaw and to the arch or tension wire 12. As will be appreciated in viewing FIG. 1 the brackets are attached by means of a base to the crown of the tooth with the arch wire 12 being displaced from the base of the bracket to a position overlying the gums away from the crown of the teeth. In this instance the arch wire 12 is sufficiently below the lower lips as will be described to be essentially non visible.

As seen in FIG. 2 the arch wire 12 curves about the lower jaw inside the lower lip with the attachment brackets attached to the respective teeth and connected to the wire. With this arrangement any suitable form of force, torque or leverage may be applied to the tooth to reposition or realign the tooth as desired.

Referring to FIG. 4 a detailed illustration of the attachment bracket is shown. The bracket includes a base attachment member 16 for bonding directly to a tooth or to a tooth band or the like. In addition, a band or other attachment means may be utilized in place of the pad 16. An elongated arm 18 is attached to the pad substantially at the center thereof and extends slightly outward and curves to extend along an axis that would extend it parallel to the tooth axis or surface to which the pad is attached.

An attachment clamp for attaching the device to a tension or arch wire includes a central body member 20 which is moveably mounted on the arm 18 and includes suitable means such as a screw mechanism or device 22 which when rotated by a screw driver or the like moves the bracket to selected positions along the length of the arm 18. A locking nut 24 is lockable against the bracket 20 locking it into position. The arm 18 is annealed so that it can be individually adjusted.

The clamp structure includes a bracket member 26 attached to the central body portion 20 includes an arch wire slot 28 in which an arch wire 12 fits. The slot opens outward for labial installation, and is illustrated for a rectangular cross section wire but may utilize a wire of any cross sectional configuration. A rotating hollow hub member 30 is mounted on the slotted shaft 26 and includes an open side for receiving or permitting the wire to pass through into and out of slot 28. Rotation of the hub for misalignment of the slots locks the wire into position relative to the bracket. Preferably the slot 28 opens downward or toward the base of the bracket as shown in FIG. 6 for lingual installation such that with any position of the bracket the slot can be opened to insert or remove the tension or arch wire as required.

The orthodontic brackets may be positioned either on the labial side (outside) of the teeth as shown in FIGS. 1 and 2 or lingual side (inside) of the teeth as shown in FIG. 4. These brackets may be attached as by bonding the base 16 directly to the surface of the tooth with the arm extending or lying generally parallel to the axis of the tooth for positioning the clamp portion of the bracket in a position away from the crown of the tooth adjacent or beyond the gums away from the tooth. This permits the arch wire to be positioned away from the surface of the teeth and at a position closer to the root of the tooth for placing the center force at or adjacent to the root of the tooth for location or centering of the force thereat.

Turning to FIG. 5 an orthodontic bracket 14 is shown attached to a tooth 32 in a lower gum 34 of a mouth. As shown in FIG. 5 the wire clamp of the bracket 20 is positioned such that the wire slot 28 is just below the gum line between the tooth 32 and gum 34. This places the wire and the main portion of the bracket at a position beneath the lower lip such that it is completely covered by the lower lip. In addition, as explained, this places the tension wire at a position closer to the pivot point or root of tooth 32 for closely controlling the force applied thereto.

Referring now to FIG. 6 an orthodontic bracket 14 is shown attached to an upper tooth 38 on the lingual (tongue) side of the teeth. This places the bracket in a completely invisible position and, again with the arm 18 of the bracket extending from the base up along an axis substantially parallel to the axis of the tooth 38. The clamp portion of the bracket 20 is positioned offset from the base 16 at a position which may be close to or beyond the gum line of the gum 40 in the upper jaw. As in the previous embodiment or arrangement the tension wire slot 28 is opened downward to the opening of the mouth to permit the insertion and removal of a tension wire 42 as desired.

Referring to FIG. 7 details of an adjustment structure for the wire lock is illustrated. The bracket member 20 is mounted for movement along the arm 18. A screw device 22 including a screw 46 is rotatably mounted in a bore 48 in the bracket member 20. Threads on the outer surface of the screw 46 engage screw segments 50 that are formed on and extend along the shaft 18. The arm 18 includes a flat section 52 along adjacent the segments 50 engageable by the bracket 20 to prevent rotation thereof on the arm 18. Other suitable adjusting means may be provided for adjusting the bracket 20 on the arm 18.

The outer end of the arm 18 may be provided with means such as a ball 54 for preventing the bracket 20 from sliding off the end of the arm. The ball or knob 54 also eliminates short edges on the arm.

While I have illustrated and described my invention by means of specific embodiments it is to be understood that numerous changes and modifications may be made therein without departing from the spirit and scope of the invention as defined in the appended claims.

I claim:

1. An orthodontic appliance, comprising:
 a base member having a generally planar surface for attachment to a tooth,
 an elongated arm secured at an inner end to said base and extending generally parallel to said planar surface for extending generally parallel to a tooth to which the base is attached and terminating at an outer end at a position offset from said base and from the crown of the tooth, and
 a wire lock comprising a wire receiving slot and closure means for closing said slot mounted on the outer end of said arm for attachment of an arch wire.

2. The orthodontic appliance of claim 1 wherein said lock is adjustable along said arm.

3. The orthodontic appliance of claim 1 wherein said base is a bonding pad for attachment to a tooth.

4. The orthodontic appliance of claim 3 wherein said wire lock is adjustable along said arm.

5. The orthodontic appliance of claim 2 including adjusting means for moving said lock along said arm.

6. The orthodontic appliance of claim 5 wherein said adjusting means comprises a rotatable screw carried by said lock and drivingly engaging teeth on said arm.

7. The orthodontic appliance of claim 4 wherein said wire lock comprises a wire receiving slot that opens toward said base.

8. The orthodontic appliance of claim 4 wherein said wire lock opens outward away from said arm.

9. An orthodontic bracket comprising:
 a base having a generally flat planar surface for attachment to a tooth,
 an elongated arm secured at an inner end to said base and extending generally parallel to said planar surface for extending generally parallel to the axis of a tooth to which the base is attached and terminating at an outer end at a position offset from said base for extending beyond the gum line from the crown of the tooth, and
 a wire lock comprising a wire receiving slot and closure means for closing said slot mounted on the outer end of said arm for attachment of an arch wire so that said lock and said wire may be positioned beyond the gum line from a tooth and behind the lips.

10. The orthodontic appliance of claim 9 wherein said lock is adjustable along said arm.

11. The orthodontic appliance of claim 10 wherein said base is a bonding pad for attachment to a tooth.

12. The orthopedic appliance of claim 9 wherein said wire lock is adjustable along said arm by means of a rotatable screw mounted on said lock and threadably engaging said arm.

13. The orthopedic appliance of claim 10 wherein said arm comprises a threaded portion; and
 said lock comprises threaded means threadably engaging said threaded portion for adjusting the position of said lock along said arm.

* * * * *